United States Patent
Lim et al.

(10) Patent No.: US 11,707,400 B2
(45) Date of Patent: Jul. 25, 2023

(54) WEARABLE DEVICE AND OPERATION METHOD OF THE WEARABLE DEVICE

(71) Applicant: Samsung Electronics Co., Ltd., Suwon-si (KR)

(72) Inventors: Bokman Lim, Hwaseong-si (KR); Youn Baek Lee, Yongin-si (KR); Jongwon Lee, Suwon-si (KR); Jusuk Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 520 days.

(21) Appl. No.: 16/810,247

(22) Filed: Mar. 5, 2020

(65) Prior Publication Data
US 2021/0085553 A1   Mar. 25, 2021

(30) Foreign Application Priority Data
Sep. 24, 2019   (KR) .................. 10-2019-0117551

(51) Int. Cl.
*A61H 3/00* (2006.01)
*A61B 5/11* (2006.01)
*A61B 5/00* (2006.01)

(52) U.S. Cl.
CPC ............ *A61H 3/00* (2013.01); *A61B 5/112* (2013.01); *A61B 5/4836* (2013.01);
(Continued)

(58) Field of Classification Search
CPC ............ A61H 3/00; A61H 2201/165; A61H 2201/5007; A61H 2201/5069; A61H 2003/007; A61H 2201/1215; A61H 2201/1628; A61H 2201/1642; A61H 2201/1652; A61H 2201/5005;
(Continued)

(56) References Cited

U.S. PATENT DOCUMENTS

| 8,418,704 | B1 | 4/2013 | Teeters |
| 2013/0261766 | A1* | 10/2013 | Langlois ............... A61F 2/80 623/33 |
| 2015/0127118 | A1 | 5/2015 | Herr et al. |
| 2015/0265428 | A1 | 9/2015 | Akiba |
| 2016/0045385 | A1* | 2/2016 | Aguirre-Ollinger ...................... A61H 1/0244 623/24 |

(Continued)

FOREIGN PATENT DOCUMENTS

| CN | 106142056 A | 11/2016 |
| EP | 3677237 A1 | 7/2020 |

(Continued)

OTHER PUBLICATIONS

Extended European Search Report dated Feb. 22, 2021 for corresponding European Application No. 20197783.2.

*Primary Examiner* — Amanda K Hulbert
*Assistant Examiner* — Natasha Patel
(74) *Attorney, Agent, or Firm* — Harness, Dickey & Pierce, P.L.C.

(57) ABSTRACT

A wearable device is disclosed. The wearable device may process a state variable defined based on motion information of a user, determine an interactive mode of the wearable device based on a gain associated with a magnitude of a torque of the wearable device, select a motion type from among motion types of the determined interactive mode based on a gait parameter of the user, determine a control factor for the torque based on the selected motion type, and generate the torque based on the processed state variable, the gain, and the determined control factor.

24 Claims, 11 Drawing Sheets

(52) U.S. Cl.
CPC ...... *A61B 5/7203* (2013.01); *A61H 2201/165* (2013.01); *A61H 2201/5007* (2013.01); *A61H 2201/5069* (2013.01)

(58) Field of Classification Search
CPC .......... A61H 1/0244; A61H 2201/5064; A61H 2203/0406; A61H 1/0237; A61H 1/024; A61H 2201/1207; A61H 2201/5061; A61H 2201/5084; A61H 2230/625; A61H 2201/50; A61B 5/112; A61B 5/4836; A61B 5/7203; A61B 5/6823; A61B 5/6828; A61B 5/1121; A61B 5/6802; A61B 5/6829; A63B 69/0028; A63B 21/065; A63B 2220/836; G06F 3/011; G16H 20/30; B25J 9/0006
See application file for complete search history.

(56) References Cited

U.S. PATENT DOCUMENTS

| | | | |
|---|---|---|---|
| 2016/0338897 A1 | 11/2016 | Takenaka et al. | |
| 2017/0202724 A1 | 7/2017 | De Rossi et al. | |
| 2018/0008502 A1* | 1/2018 | Asbeck | A61F 5/01 |
| 2018/0360347 A1* | 12/2018 | Lim | A61H 3/00 |
| 2019/0046078 A1 | 2/2019 | Lim et al. | |
| 2019/0160321 A1* | 5/2019 | Ozsecen | A61H 3/00 |

FOREIGN PATENT DOCUMENTS

| | | |
|---|---|---|
| JP | 2010-063813 A | 3/2010 |
| JP | 6148766 B1 | 6/2017 |
| KR | 20160098354 A | 8/2016 |
| KR | 10-2017-0019175 A | 2/2017 |
| WO | WO-2012/100250 A1 | 7/2012 |
| WO | WO-2015/080596 A1 | 6/2015 |
| WO | WO-2016/128877 A1 | 8/2016 |

* cited by examiner

WEARABLE DEVICE AND OPERATION METHOD OF THE WEARABLE DEVICE

CROSS-REFERENCE TO RELATED APPLICATION

This application claims priority under 35 U.S.C. § 119 to Korean Patent Application No. 10-2019-0117551 filed on Sep. 24, 2019, in the Korean Intellectual Property Office, the entire contents of which are incorporated herein by reference in their entirety.

BACKGROUND

1. Field

At least one example embodiment relates to a wearable device.

2. Description of the Related Art

A recent issue of aging societies has contributed to a growing number of people who experience inconvenience and pain from reduced muscular strength or joint problems due to aging. Thus, there is a growing interest in walking assistance devices that enable elderly users or patients with reduced muscular strength or joint problems to walk with less effort. In addition, exercise assistance devices that may help increase muscular strength of human bodies are under development.

SUMMARY

Some example embodiments relate to an operation method of a wearable device.

In some example embodiment, the operation method may include processing a state variable defined based on motion information of a user, determining an interactive mode of the wearable device based on a gain associated with a magnitude of a torque of the wearable device, selecting a motion type from among motion types of the determined interactive mode based on a gait parameter of the user, determining a control factor for the torque based on the selected motion type, and generating the torque based on the processed state variable, the gain, and the determined control factor.

The processing of the state variable may include smoothing the state variable.

In response to the gain being greater than or equal to a reference value and being a positive number, the determining of the interactive mode may include selecting a first interactive mode that assists the user in a movement of the user. In response to the gain being greater than or equal to the reference value and being a negative number, the determining of the interactive mode may include selecting a second interactive mode that applies resistance to a movement of the user. In response to the gain being less than the reference value, the determining of the interactive mode may include selecting a third interactive mode that applies high resistance to a movement of the user.

In response to a first gait feature value in the gait parameter being less than or equal to a first threshold value, the selecting of the motion type may include determining the motion type of the wearable device to be a walk motion type. In response to the first gait feature value being greater than the first threshold value and less than or equal to a second threshold value, the selecting of the motion type may include determining the motion type to be a walk-to-run motion type. In response to the first gait feature value being greater than the second threshold value, the selecting of the motion type may include determining the motion type to be a run motion type.

The first gait feature value may include a cadence of the user.

In response to a second gait feature value in the gait parameter being greater than a third threshold value, the selecting of the motion type may include determining the motion type of the wearable device to be a high-resistance motion type. In response to the second gait feature value being less than a fourth threshold value, the selecting of the motion type may include determining the motion type to be a slow motion type.

The second gait feature value may include a mean value of angular curve lengths of both hip joints of the user during a preset period of time.

In response to a motion type change event occurring by the selecting of the motion type from among the motion types, the determining of the control factor may include adjusting at least one of a smoothing factor to be used to smooth a signal obtained by sensing a movement of the user, or a delay in output timing of the torque.

In response to the motion type change event occurring by the selecting of the walk motion type from among the motion types, the adjusting may include decreasing the smoothing factor and increasing the delay.

In response to the motion type change event occurring by the selecting of the run motion type from among the motion types, the adjusting may include increasing the smoothing factor and decreasing the delay.

The generating of the torque may include applying, to the processed state variable, the gain, the determined control factor, and a compensation factor, and generating the torque based on a result of the applying.

The motion information may include angles of both hip joints of the user.

Some example embodiments relate to a wearable device.

In some example embodiment, the wearable device may include a controller configured to process a state variable defined based on motion information of a user, determine an interactive mode of the wearable device based on a gain associated with a magnitude of a torque of the wearable device, select a motion type from among motion types of the determined interactive mode based on a gait parameter of the user, determine a control factor for the torque based on the selected motion type, and control a driver based on the processed state variable, the gain, and the determined control factor, and the driver configured to generate the torque under the control of the controller.

The controller may be configured to smooth the state variable.

In response to the gain being greater than or equal to a reference value and being a positive number, the controller may be configured to select a first interactive mode that assists the user in a movement of the user. In response to the gain being greater than or equal to the reference value and being a negative number, the controller may be configured to select a second interactive mode that applies resistance to a movement of the user. In response to the gain being less than the reference value, the controller may be configured to select a third interactive mode that applies high resistance to a movement of the user.

In response to a first gait feature value in the gait parameter being less than or equal to a first threshold value, the controller may be configured to determine the motion type of the wearable device to be a walk motion type. In response to the first gait feature value being greater than the first threshold value and less than or equal to a second threshold value, the controller may be configured to determine the motion type to be a walk-to-run motion type. In response to the first gait feature value being greater than the second threshold value, the controller may be configured to determine the motion type to be a run motion type.

The first gait feature value may include a cadence of the user.

In response to a second gait feature value in the gait parameter being greater than a third threshold value, the controller may be configured to determine the motion type of the wearable device to be a high-resistance motion type. In response to the second gait feature value being less than a fourth threshold value, the controller may be configured to determine the motion type to be a slow motion type.

The second gait feature value may include a mean value of angular curve lengths of both hip joints of the user during a preset period of time.

In response to a motion type change event occurring by the selecting of the motion type from among the motion types, the controller may be configured to adjust at least one of a smoothing factor to be used to smooth a signal obtained by sensing a movement of the user, or a delay in output timing of the torque.

In response to the motion type change event occurring by the selecting of the walk motion type from among the motion types, the controller may be configured to decrease the smoothing factor and increase the delay.

In response to the motion type change event occurring by the selecting of the run motion type from among the motion types, the controller may be configured to increase the smoothing factor and decrease the delay.

The controller may be configured to apply, to the processed state variable, the gain, the determined control factor, and a compensation factor.

The motion information may include angles of both hip joints of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
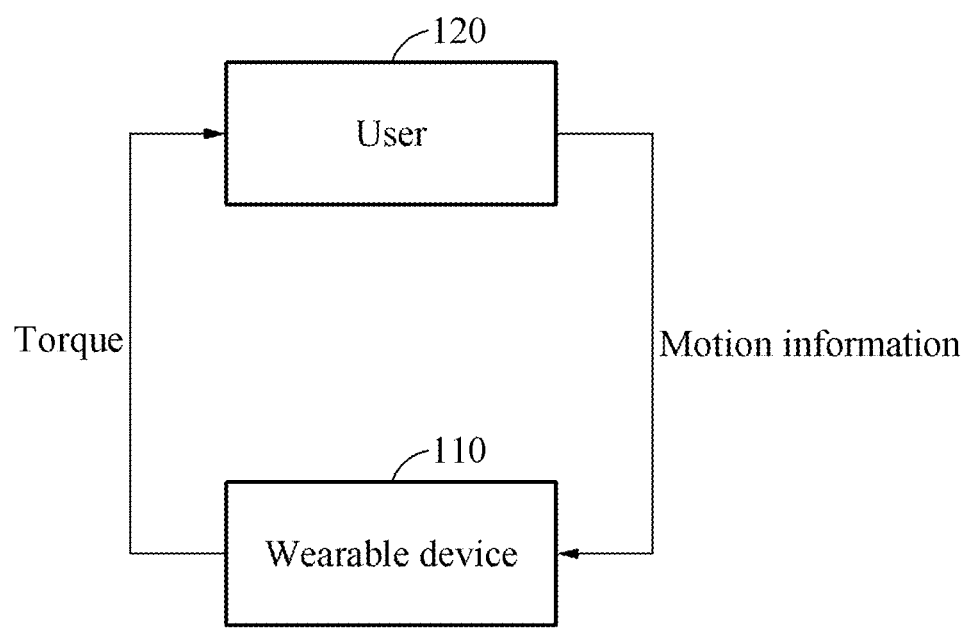
FIGS. 1 through 3 are diagrams illustrating an example of a wearable device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms, including technical and scientific terms, used herein have the same meaning as commonly understood by one of ordinary skill in the art to which the disclosure of this application pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Various example embodiments will now be described more fully with reference to the accompanying drawings in which some example embodiments are shown. In the drawings, the thicknesses of layers and regions are exaggerated for clarity.

Hereinafter, examples will be described in detail with reference to the accompanying drawings, and like reference numerals in the drawings refer to like elements throughout.

Figure 2:
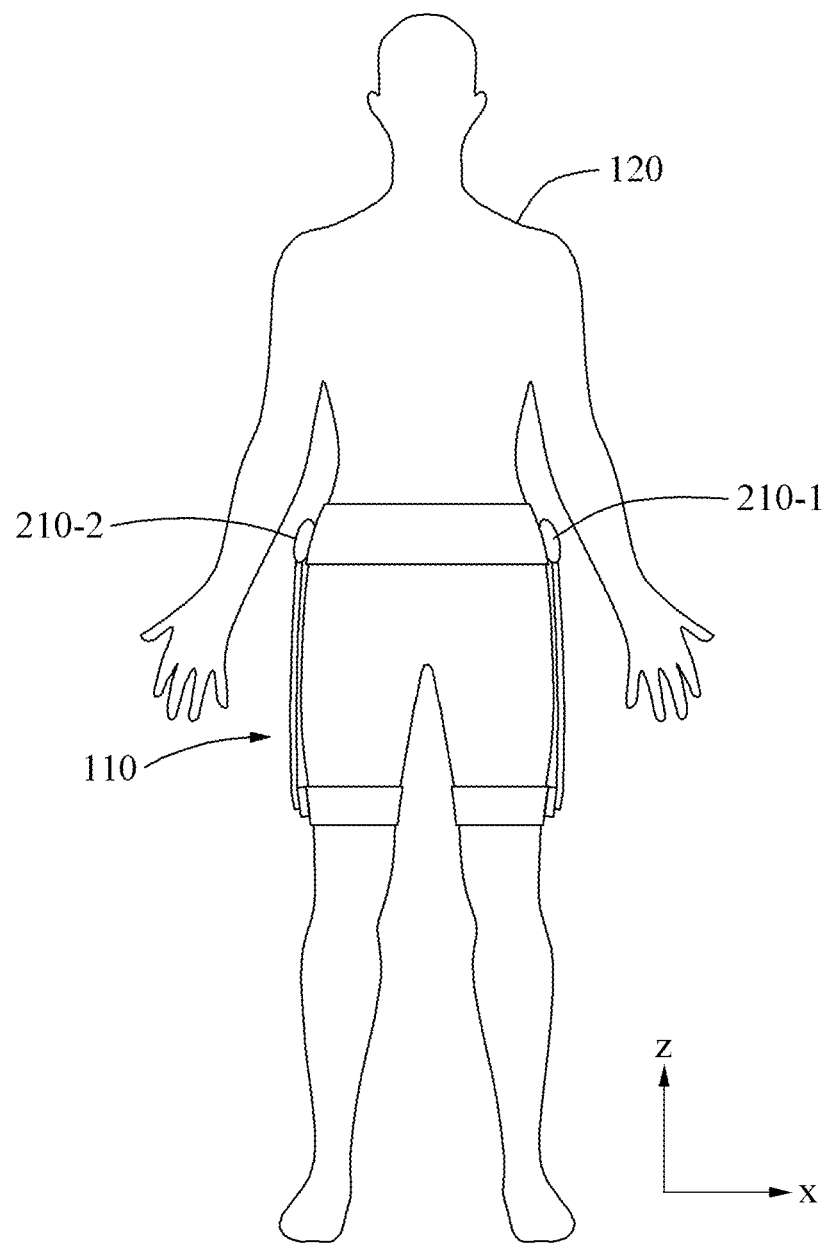
Figure 3:
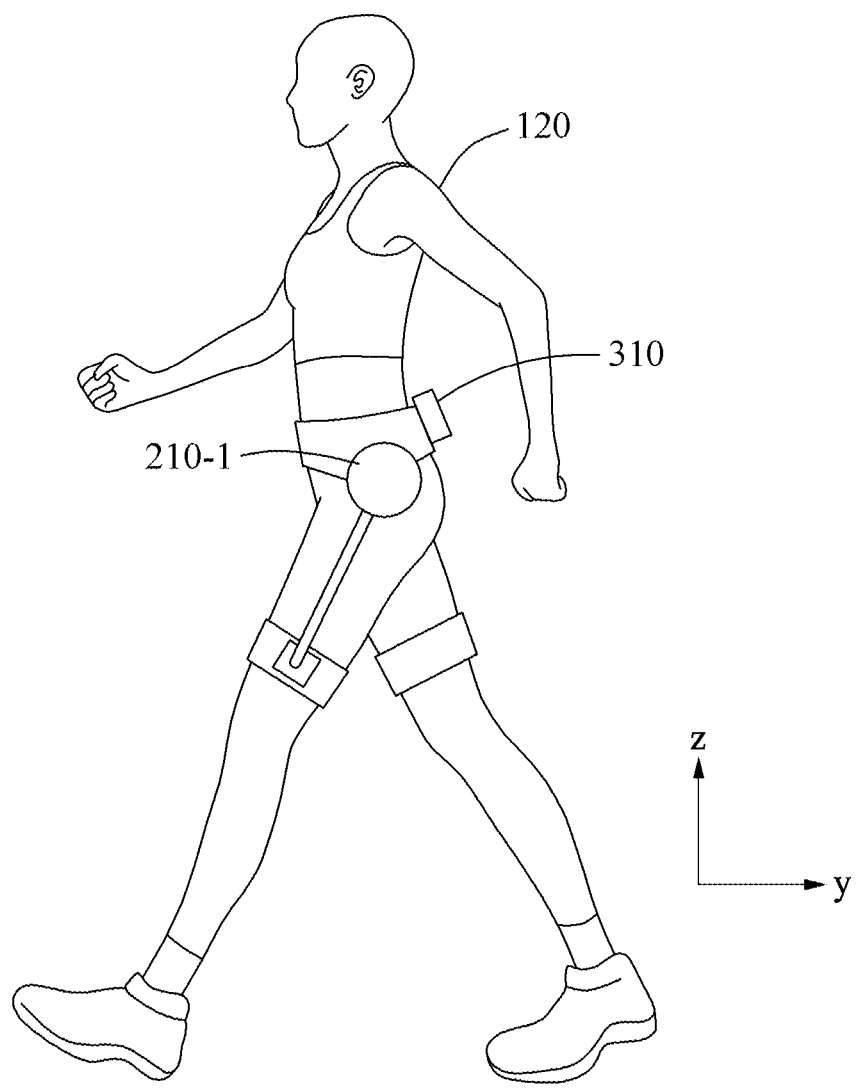

FIGS. 1 through 3 are diagrams illustrating an example of a wearable device according to at least one example embodiment.

Referring to FIG. 1, a wearable device 110 may sense or obtain motion information of a user 120 and generate a torque based on the sensed or obtained motion information and various factors. For example, the wearable device 110 may generate an assistance torque to assist the user 120 in walking. For another example, the wearable device 110 may generate a resistance torque to apply resistance to the user 120 while walking. The generating of a torque of the wearable device 110 will be described hereinafter in greater detail with reference to FIG. 4.

The wearable device 110 may be provided in a hip type to be worn on a hip joint or a thigh of the user 120, an ankle type to be worn on an ankle of the user 120, or a knee type to be worn on a knee of the user 120, for example. However, a type of the wearable device 110 is not limited to the examples described in the foregoing. The wearable device 110 illustrated in FIGS. 2 and 3 is of a hip type.

Referring to FIGS. 2 and 3, drivers 210-1 and 210-2 of the wearable device 110 are positioned around hip joints of the user 120, and a controller 310 of the wearable device 110 is positioned around a waist of the user 120. That is, the wearable device 110 of a hip type may be designed such that the drivers 210-1 and 210-2 are positioned around the hip joints of the user 120 and the controller 310 is positioned around the waist of the user 120. However, positions of the drivers 210-1 and 210-2 and the controller 310 are not limited to the example positions illustrated in FIGS. 2 and 3.

FIGS. 4 through 7 are diagrams illustrating an example of an operation of the wearable device 110 according to at least one example embodiment.

Figure 4:
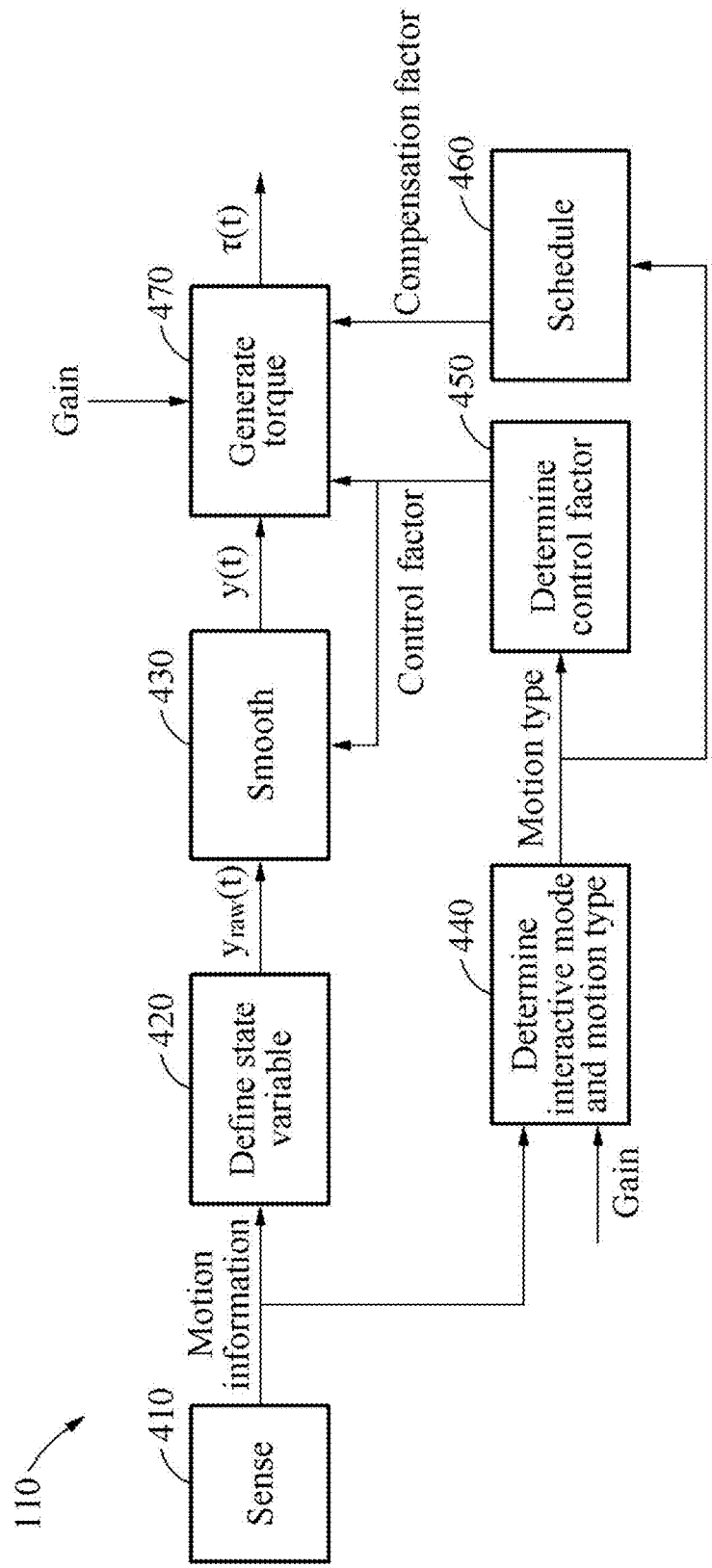
FIGS. 4 through 7 are diagrams illustrating an example of an operation of a wearable device according to at least one example embodiment.
Figure 5:
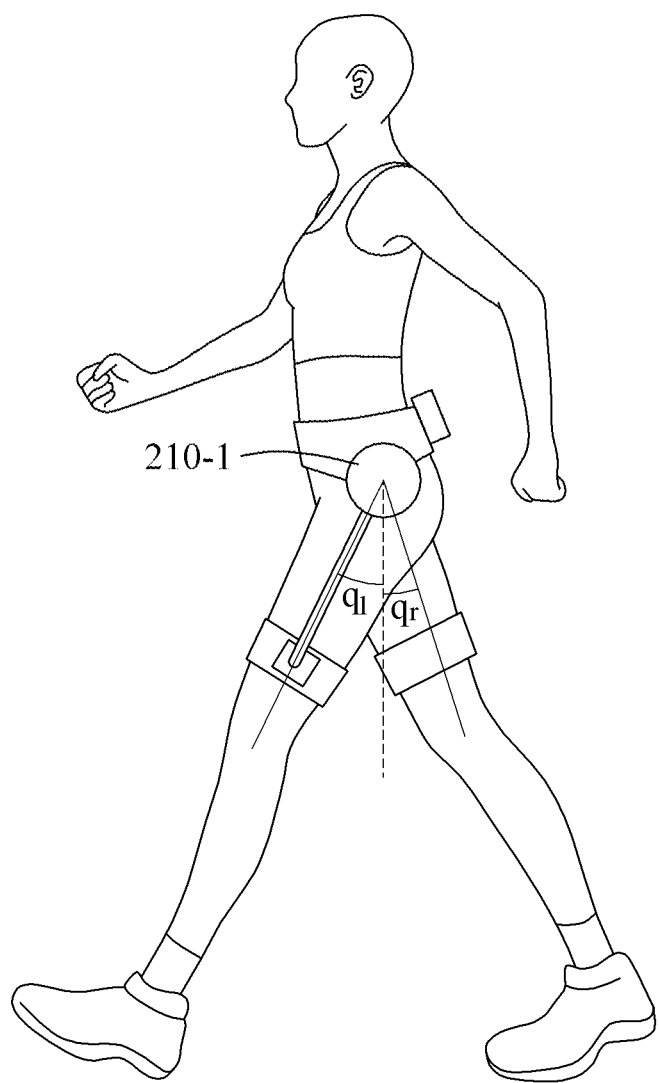

Referring to FIG. 4, in operation 410, the wearable device 110 senses a motion of the user 120 using a sensor. That is, the wearable device 110 obtains motion information of the user 120. The motion information may include, for example, angles of both hip joints of the user 120. As illustrated in FIG. 5, the wearable device 110 senses or obtains an angle $q_l(t)$ of a left hip joint of the user 120 using an encoder positioned around the driver 210-1, and senses or obtains an angle $q_r(t)$ of a right hip joint of the user 120 using an encoder positioned around the driver 210-2. When a left leg of the user 120 moves forward as illustrated in FIG. 5, the angle $q_l(t)$ of the left hip joint may be less than 0 and the angle $q_r(t)$ of the right hip joint may be greater than 0. However, according to an example, the angle $q_l(t)$ of the left hip joint may be greater than 0 and the angle $q_r(t)$ of the right hip joint may be less than 0.

Referring back to FIG. 4, in operation 420, the wearable device 110 defines a state variable. For example, the wearable device 110 defines a state variable $y_{raw}(t)$ corresponding to a difference between $\sin(q_r(t))$ and $\sin(q_l(t))$.

In operation 430, the wearable device 110 smooths the state variable $y_{raw}(t)$. Through the smoothing, noise may be removed from the state variable $y_{raw}(t)$ and a waveform of the state variable $y_{raw}(t)$ may be smoothed. For example, the wearable device 110 performs low-pass filtering on the state variable $y_{raw}(t)$. Equation 1 represents an example of a result of the smoothing or a result of the low-pass filtering.

$$y(t)=(1-\alpha)y(t_{prv})+\alpha y_{raw}(t), (0<\alpha<1) \qquad \text{[Equation 1]}$$

In Equation 1, y(t) denotes a smoothing result. In addition, α denotes a smoothing factor, and $y(t_{prv})$ denotes a previous smoothing result.

The smoothing result represented by Equation 1 is provided merely as an example, and thus the smoothing result is not limited to what is represented by Equation 1 above. The smoothing result may vary based on a type of smoothing method, or a type of low-pass filter (LPF).

In operation 440, the wearable device 110 determines an interactive mode and a motion type of the wearable device 110 based on the motion information and a gain κ. The motion information may include, for example, an angle $q_l(t)$ of a left hip joint of the user 120 and an angle $q_r(t)$ of a right hip joint of the user 120. The gain κ refers to a factor associated with a magnitude of a torque, and may be a positive or negative number. In addition, the gain κ may be received as an input from the user 120. For example, the user 120 may input the gain κ to a user interface (UI) device, for example, a tablet personal computer (PC), a smartphone, and the like, and the wearable device 110 may receive the gain κ from the UI device. According to an example, the user 120 may input the gain κ to the wearable device 110.

In an example, the wearable device 110 may determine one among a plurality of interactive modes based on the gain κ. The interactive modes may be classified based on a type of a torque or force that is output by the wearable device 110 to the user 120. For example, the interactive modes may include a first interactive mode that assists the user 120 in a movement of the user 120, a second interactive mode that applies resistance to a movement of the user 120, and a third interactive mode that applies high resistance to a movement of the user 120.

In an example, the wearable device 110 may determine one among a plurality of motion types of the determined interactive mode based on the motion information. The motion types may be classified based on a speed of a movement of the user 120. For example, motion types of the first and second interactive modes may be different from motion types of the third interactive mode. The first and second interactive modes may include, for example, a walk motion type, a walk-to-run motion type, and a run motion type. The third interactive mode may include a high-resistance motion type and a slow motion type.

The determining of an interactive mode and a motion type will be described hereinafter in greater detail with reference to FIG. 6.

Figure 6:
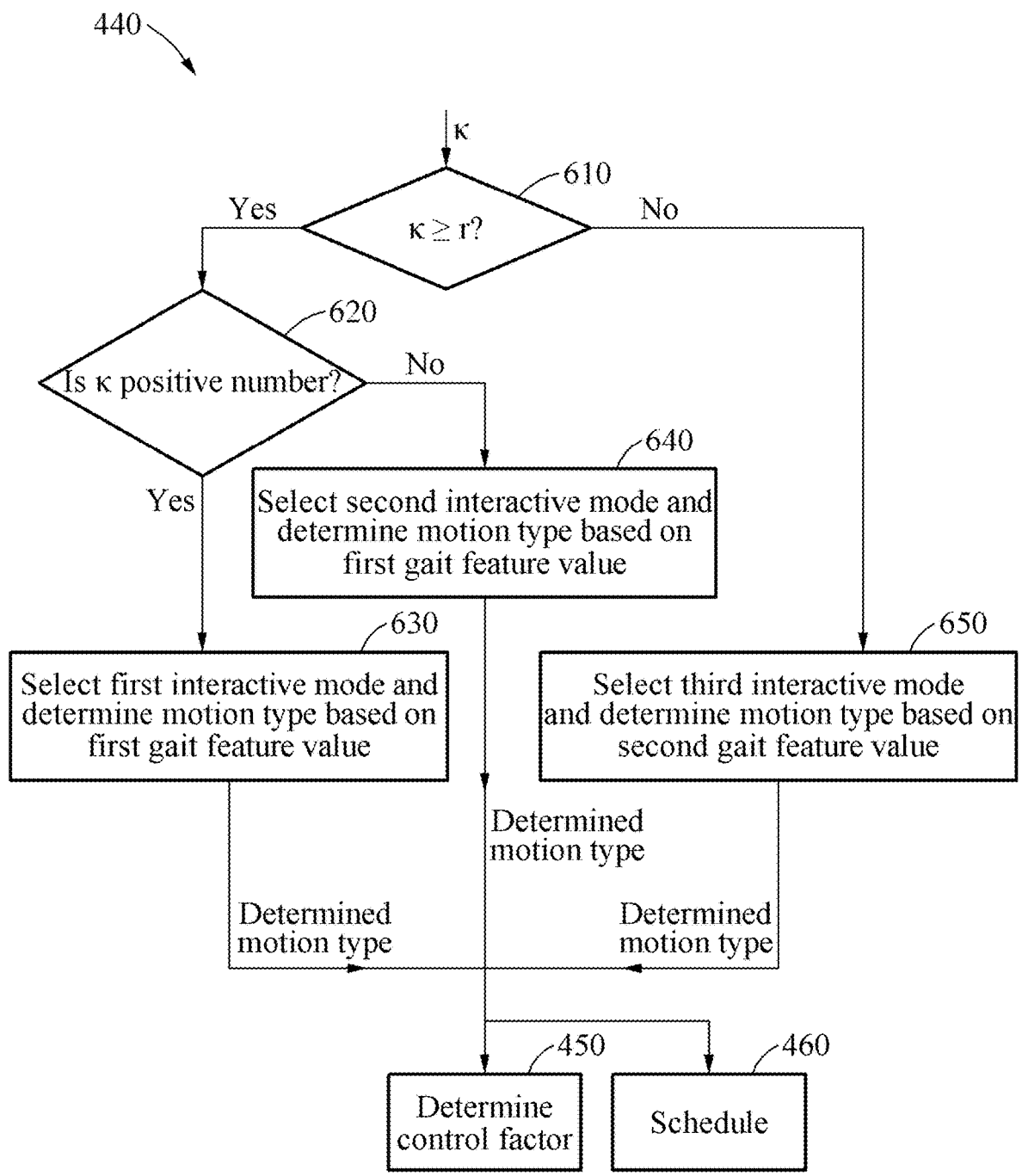

Referring to FIG. 6, in operation 610, the wearable device 110 determines whether the gain κ is greater than or equal to a reference value r, or not.

In operation 620, in response to a determination that the gain κ is greater than or equal to the reference value r, the wearable device 110 determines whether the gain κ is a positive number or not.

In operation 630, in response to a determination that the gain κ is a positive number, the wearable device 110 selects the first interactive mode and determines a motion type of the wearable device 110 based on a first gait feature value. The first gait feature value may include a cadence of the user 120. The cadence may be calculated based on gait information of the user 120 that includes, for example, a time used when the user 120 walks two steps forward and a walking distance when the user 120 walks the two steps forward.

For example, when the reference value r is −5 (r=−5) and the gain κ is +5 (κ=+5), the wearable device 110 selects the first interactive mode. In addition, when the first gait feature value is less than or equal to a first threshold value (e.g., 120 which will be described hereinafter with reference to FIG. 9), the wearable device 110 determines the motion type of the wearable device 110 to be the walk motion type. When the first gait feature value is greater than the first threshold value and less than or equal to a second threshold value (e.g., 140 which will be described hereinafter with reference to FIG. 9), the wearable device 110 determines the motion type of the wearable device 110 to be the walk-to-run motion type. When the first gait feature value is greater than the second threshold value, the wearable device 110 determines the motion type of the wearable device 110 to be the run motion type. That is, when the cadence of the user 120 is less than a preset range, the wearable device 110 may determine that the user 120 is walking and select the walk motion type. When the cadence of the user 120 is in the preset range, the wearable device 110 may determine that the user 120 is walking relatively fast and select the walk-to-run motion type. When the cadence of the user 120 is greater than the preset range, the wearable device 110 may determine that the user 120 is running and select the run motion type.

In this example, the gain κ is a positive number, and thus the wearable device 110 may output a torque that assists the user 120 in his/her movement irrespective of a motion type to be selected in the first interactive mode. Although to be described hereinafter, a control factor may vary for each motion type, and thus a magnitude of an assistance torque may increase in sequential order starting from the walk motion type to the walk-to-run motion type and then to the run motion type.

In operation 640, in response to a determination that the gain κ is a negative number, the wearable device 110 selects the second interactive mode and determines the motion type of the wearable device 110 based on the first gait feature value. For example, when the reference value r is −5 (r=−5) and the gain κ is −3 (κ=−3), the wearable device 110 selects the second interactive mode. As described above in relation to operation 630, the wearable device 110 determines one among the walk motion type, the walk-to-run motion type, and the run motion type based on the first gait feature value. In this example, the gain κ is a negative number, and thus the wearable device 110 may output a torque that applies resistance to a movement of the user 120 irrespective of a motion type to be selected in the second interactive mode. Although to be described hereinafter, a control factor may vary for each motion type, and thus a magnitude of a resistance torque may increase in sequential order starting from the walk motion type to the walk-to-run motion type and then to the run motion type.

In operation 650, in response to a determination that the gain κ is less than the reference value r in operation 610, the wearable device 110 selects the third interactive mode and determines the motion type of the wearable device 110 based on a second gait feature value. For example, when the reference value r is −5 (r=−5) and the gain κ is −7 (k=−7), the wearable device 110 selects the third interactive mode. In addition, when the second gait feature value is greater than a third threshold value (e.g., 0.5 which will be described hereinafter with reference to FIG. 9), the wearable device 110 determines the motion type of the wearable device 110 to be the high-resistance motion type. When the second gait feature value is less than a fourth threshold value (e.g., 0.4 which will be described hereinafter with reference to FIG. 9), the wearable device 110 determines the motion type of the wearable device 110 to be the slow motion type. That is, when the second gait feature value of the user 120 is greater than the third threshold value, the wearable device 110 may select the high-resistance motion type to apply high resistance to a movement of the user 120. When the second gait feature value of the user 120 is less than the fourth threshold value, the wearable device 110 may determine that the user 120 is walking relatively slow and select the slow motion type to apply an assistance torque of a small magnitude to such a slow movement of the user 120.

The second gait feature value may refer to a value from which a gait characteristic of the user 120, for example, a walking speed, during a preset period of time may be estimated. The second gait feature value will be described hereinafter in greater detail with reference to FIG. 8.

Referring back to FIG. 4, in operation 450, the wearable device 110 determines a control factor based on the determined motion type. The control factor may include at least one of a smoothing factor α or a delay Δt associated with an output timing of a torque. Although to be described hereinafter, the control factor may affect a response characteristic of a torque, and thus be referred to as a response variable or a sensing response variable. The determining of a control factor will be described hereinafter in greater detail with reference to FIG. 7.

Figure 7:
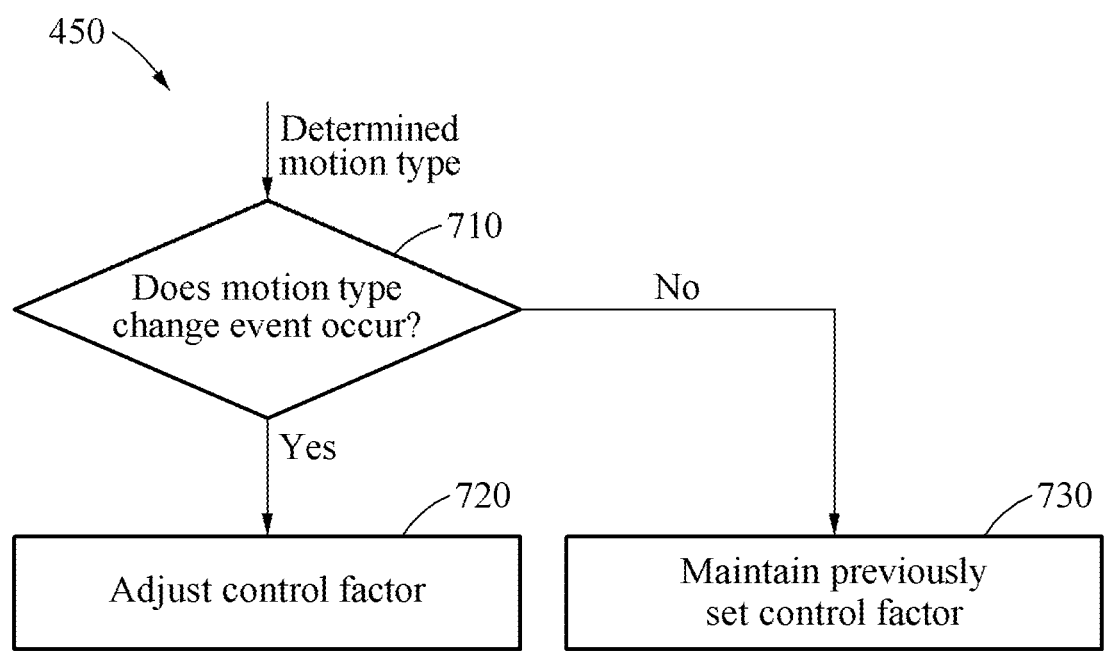

Referring to FIG. 7, in operation 710, the wearable device 110 verifies whether a motion type change event occurs. For example, the wearable device 110 verifies whether the motion type determined in operation 440 is the same as a previous motion type. In this example, when the motion type determined in operation 440 is not the same as the previous motion type, the motion type change event may occur. In contrast, when the motion type determined in operation 440 is the same as the previous motion type, the motion type change event may not occur.

In operation 720, when the motion type change event occurs, the wearable device 110 adjusts the control factor. For example, when the previous motion type is the run motion type and the walk motion type is determined in operation 440, the motion type change event occurs, and thus the wearable device 110 changes a previously set control factor, for example, a control factor corresponding to the run motion type, to a control factor corresponding to the walk motion type. In an example, each motion type and a corresponding control factor may be mapped to each other in a lookup table. The adjusting of a control factor based on a motion type will be described hereinafter in greater detail with reference to FIG. 9.

In operation 730, when the motion type change event does not occur, the wearable device 110 maintains the previously set control factor.

Referring back to FIG. 4, in operation 460, the wearable device 110 schedules a compensation factor $\kappa_{comp}$ based on the determined motion type. The compensation factor $\kappa_{comp}$ refers to a factor to be used to compensate for a magnitude of a torque. In addition, the compensation factor $\kappa_{comp}$ may be used to adjust or compensate for linear responsiveness to torque generation for each motion type.

For example, when the run motion type is determined in operation 440, the wearable device 110 may determine the compensation factor $\kappa_{comp}$ to be 1.2. When the walk motion type is determined in operation 440, the wearable device 110 may determine the compensation factor $\kappa_{comp}$ to be 1. When the high-resistance motion type is determined in operation 440, the wearable device 110 may determine the compensation factor $\kappa_{comp}$ to be 0.8. When the slow motion type is determined in operation 440, the wearable device 110 may determine the compensation factor $\kappa_{comp}$ to be $-5/\kappa$. In an example, each motion type and a corresponding compensation factor may be mapped to each other in a lookup table.

In operation 470, the wearable device 110 generates a torque based on the smoothing result y(t), the gain $\kappa$, the control factor, and the compensation factor $\kappa_{comp}$. An example of torque $\tau$(t) may be represented by Equation 2.

$$\tau(t) = \kappa \cdot \kappa_{comp} y(t - \Delta t) \quad \text{[Equation 2]}$$

For example, the wearable device 110 may generate an assistance torque in each motion type of the first interactive mode. In this example, a control factor may vary based on each motion type, and thus an assistance torque in the walk motion type may be smaller than an assistance torque in the walk-to-run motion type, and the assistance torque in the walk-to-run motion type may be smaller than an assistance torque in the run motion type, even though the gain $\kappa$ is the same in those motion types.

For another example, the wearable device 110 may generate a resistance torque in each motion type of the second interactive mode. In this example, a control factor may vary based on each motion type, and thus a resistance torque in the walk motion type may be smaller than a resistance torque in the walk-to-run motion type, and the resistance torque in the walk-to-run motion type may be smaller than a resistance torque in the run motion type, even though the gain $\kappa$ is the same in those motion types.

For still another example, wearable device 110 may generate a high-resistance torque in the high-resistance motion type of the third interactive mode. In this example, the high-resistance torque may be stronger or greater than the resistance torque in the second interactive mode. In addition, the wearable device 110 may generate an assistance torque of a relatively small magnitude to assist the user 120 in slow walking in the slow motion type of the third interactive mode.

Figure 8:
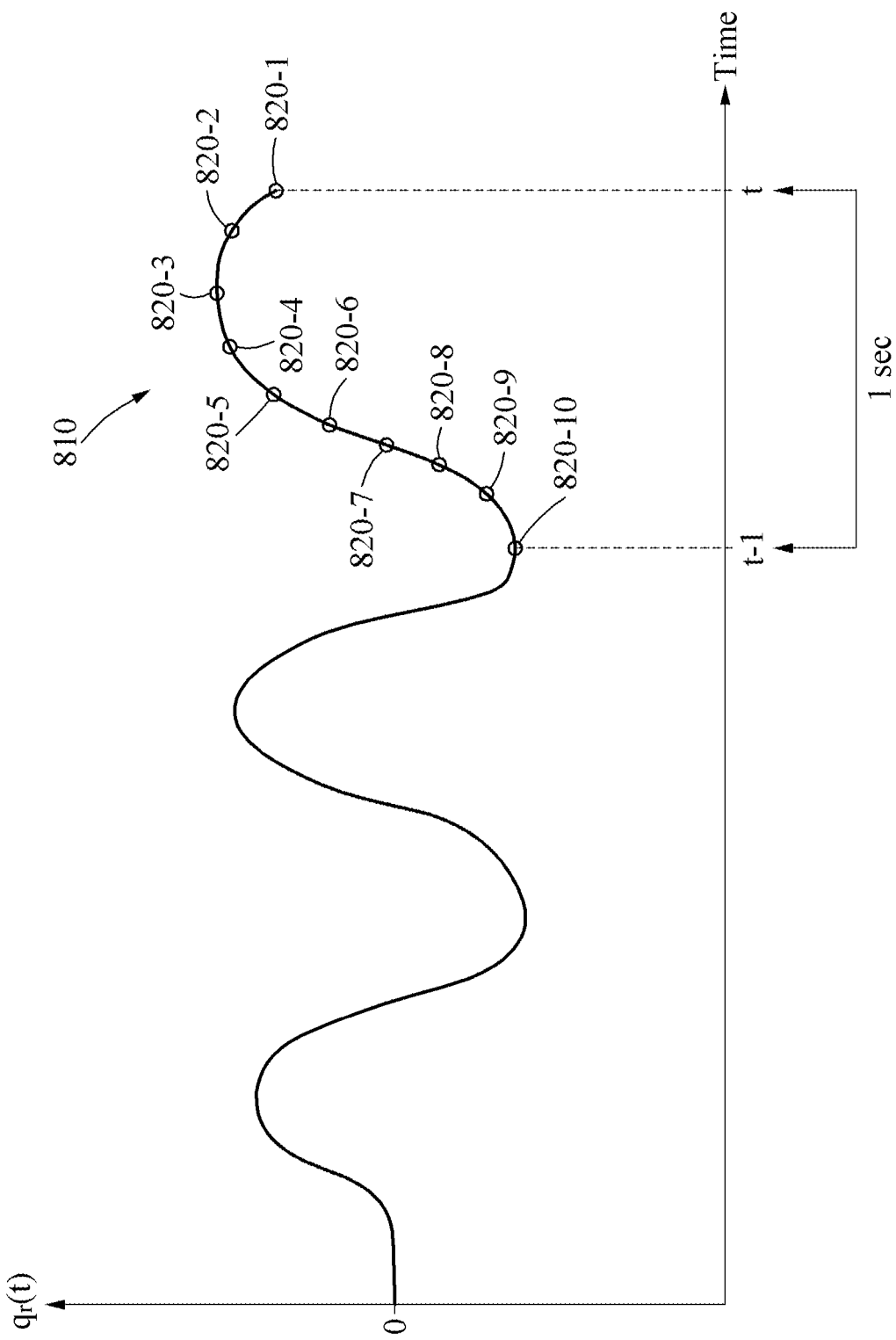
FIG. 8 is a diagram illustrating an example of a second gait feature value according to at least one example embodiment.

FIG. 8 is a diagram illustrating an example of a second gait feature value according to at least one example embodiment.

FIG. 8 illustrates an example of an angle $q_r$(t) of a right hip joint of the user 120.

A second gait feature value may be a value from which a gait characteristic of the user 120 for a desired (or, alternatively, a preset) period of time may be estimated. For example, the second gait feature value may be calculated based on each of angular curve lengths of both hip joints for a recent 1 second. In the example of FIG. 8, the wearable device 110 calculates an angular curve length $q_{r\_length}$ 810 of the angle $q_r$(t) of the right hip joint during an interval between t−1 and t as represented by Equation 3.

$$q_{length} = \int_{t-1}^{t} q(t)dt - 1 \approx \sum_{t-1}^{t} \sqrt{(t - t_{prv})^2 + (q - q_{prv})^2} - 1 \quad \text{[Equation 3]}$$

In Equation 3, $\sqrt{(t-t_{prv})^2+(q-q_{prv})^2}$ denotes a distance between a point (t, q) and a neighboring point ($t_{prv}$, $q_{prv}$). Based on Equation 3, the wearable device 110 calculates each of a distance between a point 820-1 and a point 820-2, a distance between the point 820-2 and a point 820-3, a distance between the point 820-3 and a point 820-4, a distance between the point 820-4 and a point 820-5, a distance between the point 820-5 and a point 820-6, a distance between the point 820-6 and a point 820-7, and a distance between the point 820-7 and a point 820-8, a distance between the point 820-8 and a point 820-9, and a distance between the point 820-9 and a point 820-10. The wearable device 110 calculates the angular curve length $q_{r\_length}$ 810 by subtracting 1 from a sum of the calculated distances.

Although not illustrated in FIG. 8, the wearable device 110 may also calculate an angular curve length $q_{l\_length}$ of an angle $q_l$(t) of a left hip joint of the user 120 during the interval between t−1 and t, as described above.

The wearable device 110 may calculate a mean value of the angular curve lengths $q_{r\_length}$ and $q_{l\_length}$, and determine the mean value to be the second gait feature value.

Figure 9:
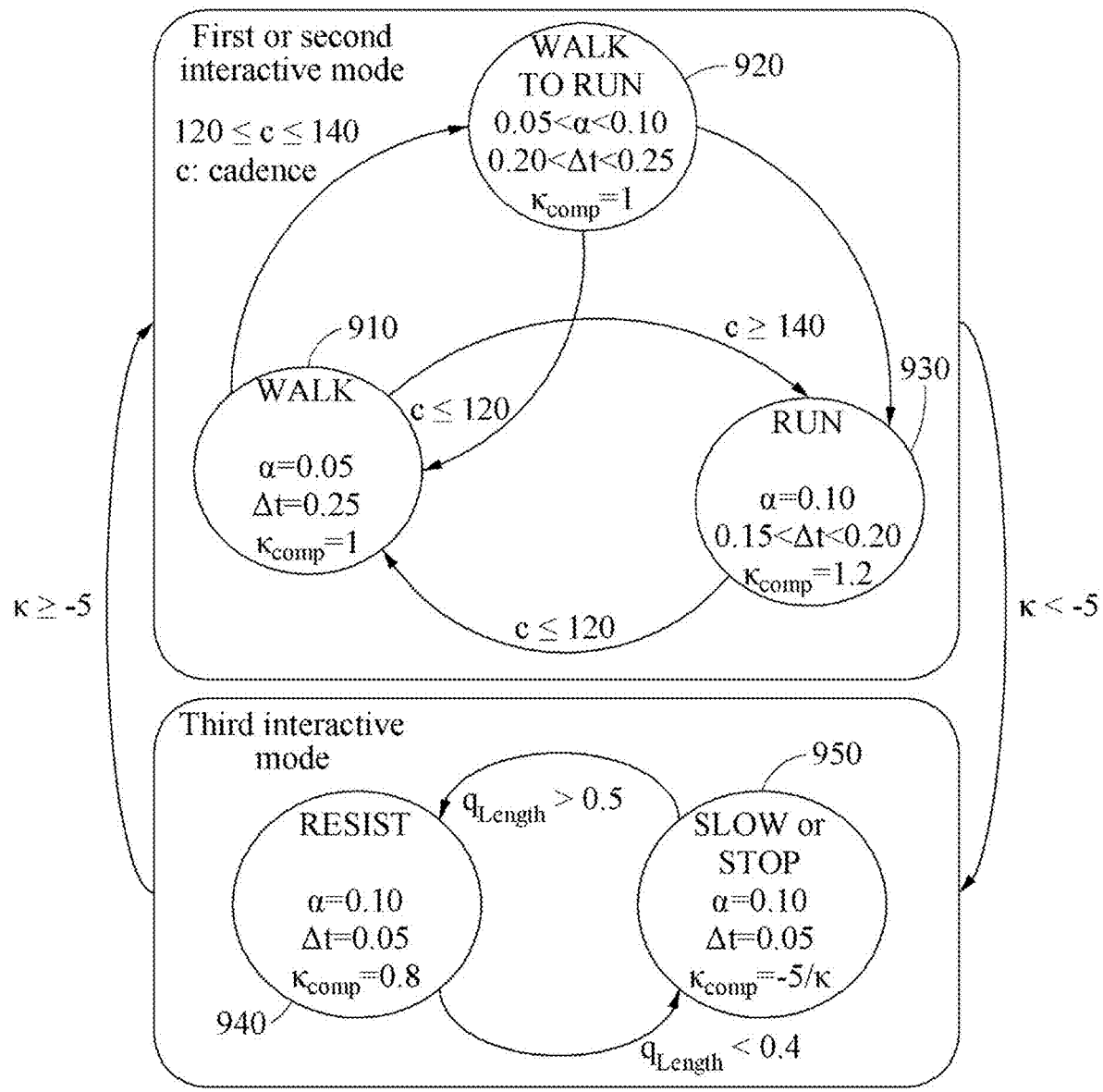
FIG. 9 is a diagram illustrating an example of a state machine of a wearable device according to at least one example embodiment.

FIG. 9 is a diagram illustrating an example of a state machine of the wearable device 110 according to at least one example embodiment.

FIG. 9 illustrates an example of a state machine when the reference value r is −5 (r=−5).

For example, when the gain $\kappa$ is greater than or equal to −5, the wearable device 110 selects the first or second interactive mode. In this example, when the gain $\kappa$ is a positive number, the wearable device 110 selects the first interactive mode. In contrast, when the gain $\kappa$ is a negative number, the wearable device 110 selects the second interactive mode. In addition, when the gain $\kappa$ is less than −5, the wearable device 110 selects the third interactive mode.

<In a Case of the Gain $\kappa$ being Greater than or Equal to −5>

Referring to FIG. 9, when a cadence of the user 120 reaches between 120 to 140 while the wearable device 110 is operating in a walk motion type 910, the wearable device 110 changes the walk motion type 910 to a walk-to-run motion type 920. As the motion type changes, the wearable device 110 adjusts a control factor. That is, since the walk-to-run motion type 920 is not the same as the walk motion type 910 which is a previous motion type, the wearable device 110 adjusts the control factor. For example, the wearable device 110 may increase a smoothing factor $\alpha$ and decrease a delay $\Delta t$. In the example of FIG. 9, the wearable device 110 increases the smoothing factor from 0.05 to a value within a range from 0.05 to 0.10, and decreases the delay from 0.25 to a value within a range from 0.20 to 0.25. Conventionally, when the cadence of the user 120 reaches between 120 to 140 while operating in a walk motion type, saturation or torque attenuation in which a torque does not increase in proportion to a walking speed may occur due to smoothing or low-pass filtering. In contrast, in one or more example embodiments, by changing to the walk-to-run motion type 920 when the cadence is reaches between 120 to 140, smoothing may be performed with the adjusted smoothing factor and a torque may be generated with the adjusted delay, and thus the saturation may be reduced or minimized, and an attenuated amount of the torque may be compensated for.

In the walk-to-run motion type 920, the smoothing factor and the delay may be set values within respective ranges. However, the values are not limited to such illustrated examples. For example, in the walk-to-run motion type 920, the smoothing factor and the delay may be values matched to a cadence of the user 120 within respective ranges. In this example, when the cadence of the user 120 is 120, the smoothing factor may be 0.055 and the delay may be 0.205. When the cadence of the user 120 is 130, the smoothing factor may be 0.075 and the delay may be 0.225. When the cadence of the user 120 is 140, the smoothing factor may be 0.095 and the delay may be 0.245.

When the cadence of the user 120 reaches 140 while the wearable device 110 is operating in the walk motion type 910, the wearable device 110 changes the walk motion type 910 to a run motion type 930. As the motion type changes, the wearable device 110 adjusts a control factor. For example, the wearable device 110 may increase a smoothing factor α and decrease a delay Δt. In the example of FIG. 9, the wearable device 110 increases the smoothing factor from 0.05 to 0.1 and decrease the delay from 0.25 to a value within a range from 0.15 to 0.20. In addition, the wearable device 110 adjusts a compensation factor $\kappa_{comp}$ from 1 to 1.2. Conventionally, when the cadence of the user 120 exceeds 140 while operating in walk motion type, torque attenuation may occur due to smoothing or low-pass filtering. In contrast, in one or more example embodiments, by changing to the run motion type 930 when the cadence is greater than or equal to 140, smoothing may be performed with the adjusted smoothing factor, and a torque may be generated with the adjusted delay and the adjusted compensation factor. Thus, an attenuated amount of the torque may be compensated for.

When the cadence of the user 120 reaches 120 while the wearable device 110 is operating in the walk-to-run motion type 920, the wearable device 110 changes the walk-to-run motion type 920 to the walk motion type 910. As the motion type changes, the wearable device 110 adjusts a control factor. For example, wearable device 110 may decrease a smoothing factor and increase a delay. In the example of FIG. 9, the wearable device 110 decreases the smoothing factor to 0.05 and increases the delay to 0.25.

When the cadence of the user 120 reaches 150 or greater while the wearable device 110 is operating in the walk-to-run motion type 920, the wearable device 110 changes the walk-to-run motion type 920 to the run motion type 930. As the motion type changes, the wearable device 110 adjusts a control factor. For example, the wearable device 110 may increase a smoothing factor and decrease a delay. In addition, the wearable device 110 may increase a compensation factor. When the cadence of the user 120 exceeds 140, torque attenuation may occur as described above. Thus, the wearable device 110 may perform smoothing using the adjusted smoothing factor and generate a torque using the adjusted delay and the adjusted compensation factor such that the torque attenuation may not occur when the walk-to-run motion type 920 changes to the run motion type 930.

When the cadence of the user 120 reaches 120 while the wearable device 110 is operating in the run motion type 930, the wearable device 110 changes the run motion type 930 to the walk motion type 910. As the motion type changes, the wearable device 110 adjusts a control factor. For example, the wearable device 110 may decrease a smoothing factor and increase a delay. In addition, the wearable device 110 may adjust a compensation factor from 1.2 to 1.

As described above, a control factor may vary for each of the motion types 910, 920, and 930. That is, with a same gain κ, a smoothing factor α may be adjusted to increase and a delay Δt may be adjusted to decrease, in sequential order starting from the walk motion type 910 to the walk-to-run motion type 920 and then to the run motion type 930. By adjusting the control factor as described in the foregoing, a magnitude of a torque may increase linearly and stably as a motion speed of the user 120 increases. In addition, the magnitude of the torque may increase linearly and stably as the gain increases linearly. Thus, a linear response characteristic and control stability of the wearable device 110 may be improved.

<In a Case of the Gain κ being Less than −5>

When $q_{length}$ is less than 0.4 while the wearable device 110 is operating in a high-resistance motion type 940, the wearable device 110 changes the high-resistance motion type 940 to a slow motion type 950. That is, the wearable device 110 changes the high-resistance motion type 940 to the slow motion type 950 when $q_{length}$ is less than 0.4, and the wearable device 110 maintains the high-resistance motion type 940 when $q_{length}$ is less than 0.5 and greater than or equal to 0.4 while the wearable device 110 is operating in the high-resistance motion type 940. In the example of FIG. 9, although the high-resistance motion type 940 changes to the slow motion type 950, a smoothing factor and a delay may not change. Similarly, also in a case in which the slow motion type 950 changes to the high-resistance motion type 940, the smoothing factor and the delay may not change. However, examples are not limited to what is described in the foregoing, and at least one of the smoothing factor or the delay may be configured to change in response to a change in motion type.

When a motion speed of the user 120 increases in the high-resistance motion type 940, a magnitude of a torque may also increase linearly and stably. In addition, when a gain increases linearly, the magnitude of the torque may also increase linearly and stably. Thus, in the high-resistance motion type 940, a linear response characteristic and control stability of the wearable device 110 may be improved.

As discussed above, conventionally, when the cadence of the user 120 reaches a threshold while operating in a walk motion type, saturation or torque attenuation in which a torque does not increase in proportion to a walking speed may occur due to smoothing or low-pass filtering and when the cadence of the user 120 exceeds a second threshold higher than the first threshold while operating in the walk motion type, torque attenuation may occur due to smoothing or low-pass filtering.

In contrast, in one or more example embodiments, when the gain κ is greater than the reference value, the wearable device 110 may operate in a first or second reference mode to adjust a control factor (e.g., a smoothing factor α and a delay Δt) by switching between a walking motion type 910, a walk to run motion type 920 and a run motion type 930 based on the cadence such that the smoothing factor increases α and the delay Δt decreases in sequential order as the cadence increases from the walk motion type 910 to the walk-to-run motion type 920 and then to the run motion type 930. Therefore, in the first interactive mode (i.e., the assistance mode when the gain κ is positive), a magnitude of the assistance torque may increase linearly and stably as the cadence of the user 120 increases during movement between the motion types 910-930 and, in the second interactive mode (i.e., the resistance mode when the gain κ is negative), a magnitude of the resistance torque may increase linearly and stably as the cadence of the user 120 increases during movement between the motion types 910-930, even though the gain κ remains the same in the motion types. Further, when the gain κ is less than the reference value, the wearable device 110 may operate in a third reference mode to maintain a constant control factor (e.g., the smoothing factor α and the delay Δt) in both the high-resistance motion type 940 and the slow motion type 950 such that the smoothing factor α is relatively high to generate a stronger resistance torque or relatively smaller assistance torque while the delay Δt is relatively short as compared to the second interactive mode. Thus, a linear response characteristic and control stability of the wearable device 110 may be improved.

Figure 10:
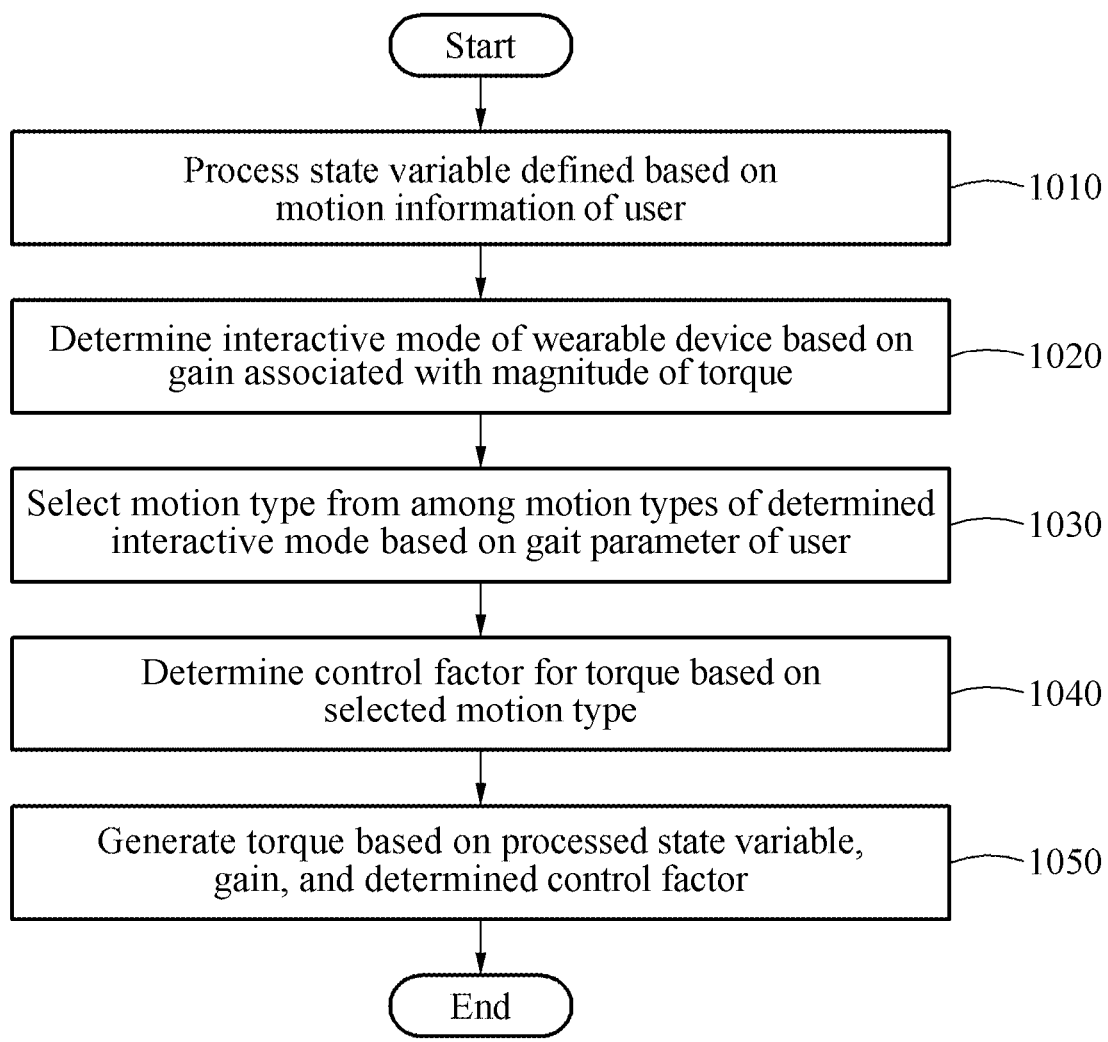
FIG. 10 is a flowchart illustrating an example of an operation method of a wearable device according to at least one example embodiment.

FIG. 10 is a flowchart illustrating an example of an operation method of the wearable device 110 according to at least one example embodiment.

Referring to FIG. 10, in operation 1010, the wearable device 110 processes a state variable defined based on motion information of the user 120. For example, the wearable device 110 may smooth a state variable $y_{raw}(t)$.

In operation 1020, the wearable device 110 determines an interactive mode of the wearable device 110 based on a gain associated with a magnitude of a torque, where the gain may be input by the user. In some other example embodiments, rather than the user inputting the gain and the controller 310 determining the interactive mode based on the input gain, the user may input the interactive mode, and the controller 310 may determine a default gain associated with the input interactive mode.

In operation 1030, the wearable device 110 selects one from among motion types of the determined interactive mode based on a gait parameter of the user 120. The gait parameter may include a plurality of gait feature values that represent gait or walking characteristics. The gait parameter may include, for example, the first and second gait feature value described above.

In operation 1040, the wearable device 110 determines a control factor for a torque based on the selected motion type. For example, the wearable device 110 may search a lookup table for a control factor corresponding to the selected motion type. For another example, the wearable device 110 may determine the control factor corresponding to the selected motion type through a regression function or a regression analysis. In an example, a control factor for each motion type may be optimized through training.

In operation 1050, the wearable device 110 generates the torque based on the processed state variable, the gain, and the determined control factor. The processed state variable may correspond to y(t) described above. The wearable device 110 may generate the torque by applying a different control factor to each motion type. Through this, a linear response characteristic and control stability of the wearable device 110 may be improved.

For a detailed description of the operation method described above with reference to FIG. 10, reference may be made to what has been described above with reference to FIGS. 1 through 9.

Figure 11:
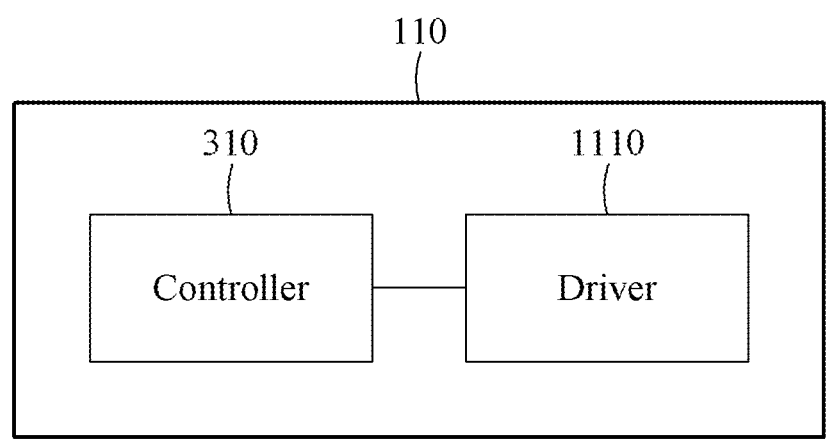
FIG. 11 is a diagram illustrating an example of a wearable device according to at least one example embodiment.

FIG. 11 is a diagram illustrating an example of the wearable device 110 according to at least one example embodiment.

Referring to FIG. 11, the wearable device 110 includes the controller 310 and a driver 1110.

Further, the wearable apparatus 110 may include a user interface (UI) device and one or more sensors. The UI device may be configured to receive an input of a gain associated with a magnitude of a torque from the user. The UI device may include various appropriate devices, for example, a switch, a knob, and a jog dial, configured to set the exercise mode. The UI device may be replaced with an external remote control or a smart device and may not need to be included in the wearable apparatus 110. The sensors may be angle sensors, for example, a potentiometer, an absolute encoder, or an incremental encoder, configured to measure an angle of a joint.

The controller 310 may be implemented in processing circuitry such as hardware including logic circuits; a hardware/software combination such as a processor executing software; or a combination thereof and memory. For example, the processing circuitry more specifically may include, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The processing circuitry may be special purpose processing circuitry that performs an overall operation of the wearable device 110 that has been described above with reference to FIGS. 1 through 10. For example, the controller 310 may process a state variable defined based on motion information of the user 120, and determine an interactive mode of the wearable device 110 based on a gain associated with a magnitude of a torque, where the gain may be input by the user 120 via a user interface (UI) device. In some other example embodiments, rather than the user inputting the gain and the controller 310 determining the interactive mode based on the input gain, the user may input the interactive mode, and the controller 310 may determine a default gain associated with the input interactive mode. In addition, the controller 310 may select one from among motion types of the determined interactive mode based on a gait parameter of the user 120, and determine a control factor for a torque based on the selected motion type. The controller 310 may then control the driver 1110 based on the processed state variable, the gain, and the determined control factor. Thus, the processing circuitry may improve the functioning of the wearable apparatus 110 itself by linearly and stably increasing a magnitude of a torque as a motion speed of the user 120 increases to improve linear response characteristic and control stability of the wearable device 110.

The driver 1110 may generate the torque under the control of the controller 310.

The wearable device 110 may include a single driver, for example, the driver 1110 as illustrated in FIG. 11, or include a plurality of drivers, for example, the drivers 210-1 and 210-2 as illustrated in FIGS. 2 and 3.

For a detailed description of the wearable device 110 described above with reference to FIG. 11, reference may be made to what has been described above with reference to FIGS. 1 through 10.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An operation method of a wearable device, the operation method comprising:
    processing a state variable to generate a processed state variable, the state variable being based on motion information of a user;
    determining an interactive mode of the wearable device as a first interactive mode or a second interactive mode based on a sign of a gain associated with a magnitude of a torque of the wearable device, the first interactive mode being a mode in which the wearable device assists a movement of the user, and the second interactive mode being a mode in which the wearable device applies a first resistance to the movement of the user;
    determining a motion type from among a plurality of motion types associated with the interactive mode based on a gait parameter of the user, the motion types being classified based on a walking speed of the user;
    determining a control factor for the torque based on the motion type; and
    generating the torque based on the processed state variable, the gain, and the control factor.

2. The operation method of claim 1, wherein the processing of the state variable comprises:
    smoothing the state variable to generate the processed state variable.

3. The operation method of claim 1, wherein the determining of the interactive mode comprises:
    selecting the first interactive mode, in response to the gain being a positive number; or
    selecting the second interactive mode, in response to the gain being a negative number.

4. The operation method of claim 1, wherein the gait parameter includes a first gait feature value, and the determining of the motion type comprises:
    determining the motion type of the wearable device to be a walk motion type, in response to the first gait feature value being less than or equal to a first threshold value;
    determining the motion type to be a walk-to-run motion type, in response to the first gait feature value being greater than the first threshold value and less than or equal to a second threshold value; or
    determining the motion type to be a run motion type, in response to the first gait feature value being greater than the second threshold value.

5. The operation method of claim 4, wherein the first gait feature value is a cadence of the user.

6. The operation method of claim 1, wherein the gait parameter includes a first gait feature value and a second gait feature value, and the determining of the motion type comprises:
    determining the motion type of the wearable device to be a resistance motion type, in response to the second gait feature value in the gait parameter being greater than a third threshold value; and
    determining the motion type to be a slow motion type, in response to the second gait feature value being less than a fourth threshold value.

7. The operation method of claim 6, wherein the second gait feature value is a mean value of angular curve lengths of hip joints of the user during a set period of time.

8. The operation method of claim 1, wherein the determining of the control factor comprises:
    adjusting at least one of a smoothing factor associated with the processing of the state variable and a delay in output timing of the torque, in response to a motion type change event occurring by the determining of the motion type.

9. The operation method of claim 8, wherein the adjusting comprises:
    decreasing the smoothing factor and increasing the delay, in response to the motion type change event occurring by determining a walk motion type from among the plurality of motion types.

10. The operation method of claim 8, wherein the adjusting comprises:
    increasing the smoothing factor and decreasing the delay, in response to the motion type change event occurring by determining a run motion type from among the plurality of motion types.

11. The operation method of claim 1, wherein the generating of the torque comprises:
    set a torque value by applying, to the processed state variable, the gain, the control factor, and a compensation factor; and
    generating the torque based on the torque value.

12. The operation method of claim 1, wherein the motion information includes angles of hip joints of the user.

13. A wearable device comprising:
a driver configured to generate a torque; and
a controller configured to,
  process a state variable to generate a processed state variable, the state variable being based on motion information of a user,
  determine an interactive mode of the wearable device as a first interactive mode or a second interactive mode based on a sign of a gain associated with a magnitude of the torque of the wearable device, the first interactive mode being a mode in which the wearable device assists the user in a movement of the user, and the second interactive mode being a mode in which the wearable device applies a first resistance to a movement of the user,
  determine a motion type from among a plurality of motion types associated with the interactive mode based on a gait parameter of the user, the motion types being classified based on a walking speed of the user,
  determine a control factor for the torque based on the motion type, and
  control the driver based on the processed state variable, the gain, and the control factor.

14. The wearable device of claim 13, wherein the controller is configured to process the state variable by smoothing the state variable to generate the processed state variable.

15. The wearable device of claim 13, wherein the controller is configured to:
  select the first interactive mode, in response to the gain being a positive number, or
  select the second interactive mode, in response to the gain being a negative number.

16. The wearable device of claim 13, wherein the gait parameter includes a first gait feature value, and the controller is configured to:
  determine the motion type of the wearable device to be a walk motion type, in response to the first gait feature value being less than or equal to a first threshold value,
  determine the motion type to be a walk-to-run motion type, in response to the first gait feature value being greater than the first threshold value and less than or equal to a second threshold value, or
  determine the motion type to be a run motion type, in response to the first gait feature value being greater than the second threshold value.

17. The wearable device of claim 16, wherein the first gait feature value is a cadence of the user.

18. The wearable device of claim 13, wherein the gait parameter includes a first gait feature value and a second gait feature value, and the controller is configured to:
  determine the motion type of the wearable device to be a resistance motion type, in response to the second gait feature value being greater than a third threshold value, and
  determine the motion type to be a slow motion type, in response to the second gait feature value being less than a fourth threshold value.

19. The wearable device of claim 18, wherein the second gait feature value is a mean value of angular curve lengths of hip joints of the user during a set period of time.

20. The wearable device of claim 13, wherein the controller is configured to:
  adjust at least one of a smoothing factor associated with the processing of the state variable or a delay in output timing of the torque, in response to a motion type change event occurring by the controller selecting the motion type.

21. The wearable device of claim 20, wherein the controller is configured to:
  decrease the smoothing factor and increase the delay, in response to the motion type change event occurring by the controller selecting a walk motion type from among the plurality of motion types.

22. The wearable device of claim 20, wherein the controller is configured to:
  increase the smoothing factor and decrease the delay, in response to the motion type change event occurring by the controller selecting a run motion type from among the plurality of motion types.

23. The wearable device of claim 13, wherein the controller is configured to:
  set a torque value by applying, to the processed state variable, the gain, the control factor, and a compensation factor.

24. The wearable device of claim 13, wherein the motion information includes angles of hip joints of the user.

* * * * *